(12) United States Patent
Yoo et al.

(10) Patent No.: US 7,943,970 B2
(45) Date of Patent: May 17, 2011

(54) METHOD OF DETECTING BIO-MOLECULES USING THE SAME FIELD EFFECT TRANSISTOR ON THE GATE SENSING SURFACE

(75) Inventors: Kyu-tae Yoo, Yongin-si (KR); Kyu-sang Lee, Yongin-si (KR); Jeo-young Shim, Yongin-si (KR); Won-seok Chung, Yongin-si (KR); Yeon-ja Cho, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 208 days.

(21) Appl. No.: 11/695,886

(22) Filed: Apr. 3, 2007

(65) Prior Publication Data

US 2007/0231211 A1    Oct. 4, 2007

(30) Foreign Application Priority Data

Apr. 3, 2006 (KR) .......................... 10-2006-0030169

(51) Int. Cl.
*G01N 27/403* (2006.01)
(52) U.S. Cl. ............ 257/253; 257/47; 257/48; 257/252; 422/82.01; 422/82.03; 422/68.1; 435/91.2
(58) Field of Classification Search .............. 257/47–48, 257/252–253; 435/91.2; 422/82.01–82.03, 422/68.1
See application file for complete search history.

(56) References Cited

U.S. PATENT DOCUMENTS

| | | | |
|---|---|---|---|
| 4,238,757 A | 12/1980 | Schenck | |
| 4,777,019 A | 10/1988 | Dandekar | |
| 5,466,348 A | 11/1995 | Holm-Kennedy | |
| 5,846,708 A | 12/1998 | Hollis et al. | |
| 6,203,981 B1 | 3/2001 | Ackley et al. | |
| 6,258,027 B1 * | 7/2001 | Sternby | 600/366 |
| 2004/0134798 A1 * | 7/2004 | Toumazou et al. | 205/793.5 |
| 2006/0011911 A1 | 1/2006 | Bockelmann et al. | |

FOREIGN PATENT DOCUMENTS

WO    03062811 A1    7/2003

OTHER PUBLICATIONS

Office Action dated Apr. 23, 2007 for Korean Application No. 10-2006-0030169.

\* cited by examiner

*Primary Examiner* — In Suk Bullock
*Assistant Examiner* — Robert Eom
(74) *Attorney, Agent, or Firm* — Cantor Colburn LLP

(57) ABSTRACT

Provided is a method of detecting the presence of a target bio-molecule or a concentration of the bio-molecule using a field effect transistor. The method includes: contacting a first sample having a first target bio-molecule with a reference electrode of a field effect transistor; measuring a first electric signal change of the field effect transistor; contacting a second sample with a sensing surface of the same field effect transistor; measuring a second electric signal change of the field effect transistor; and comparing the first electric signal with the second electric signal.

9 Claims, 3 Drawing Sheets

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: forward primer

<400> SEQUENCE: 1
tagcatatca gaaggcacac cc                                    22

<210> SEQ ID NO 2
<211> LENGTH: 23
<212> TYPE: DNA
<213> ORGANISM: Artificial Sequence
<220> FEATURE:
<223> OTHER INFORMATION: reverse primer

<400> SEQUENCE: 2
atccactcaa gagagacaac att                                   23

US 7,943,970 B2

METHOD OF DETECTING BIO-MOLECULES USING THE SAME FIELD EFFECT TRANSISTOR ON THE GATE SENSING SURFACE

CROSS-REFERENCE TO RELATED PATENT APPLICATION

This application claims the benefit of Korean Patent Application No. 10-2006-0030169, filed on Apr. 3, 2006, in the Korean Intellectual Property Office, the disclosure of which is incorporated herein in its entirety by reference.

BACKGROUND OF THE INVENTION

1. Field of the Invention

The present invention relates to a method of detecting the presence of a target bio-molecule or a concentration of the respective bio-molecules using a field effect transistor.

2. Description of the Related Art

A transistor based bio-sensor which includes a transistor is one kind of sensor that detects bio-molecules using electric signals. A semiconductor process is used to manufacture the transistor based bio-sensor, and thus the electric signals can be quickly converted in the transistor based bio-sensor. Accordingly, much research on this kind of sensor has been carried out.

U.S. Pat. No. 4,238,757 discloses a field effect transistor (FET) that can be used to detect biological reactions. Using the FET, a bio-sensor measures a current change in an inversion layer of a semiconductor resulting from changes in the surface charge concentration in order to detect an antigen-antibody reaction. By employing a bio-sensor using the FET, the presence of a protein among the bio-molecules can be detected. U.S. Pat. No. 4,777,019 discloses a sensor for measuring a hybridization of biological monomers with complementary monomers by adsorbing the biological monomers onto the surface of a gate using a FET.

U.S. Pat. No. 5,846,708 discloses a method of determining the presence of hybridization by an extinction of coupled bio-molecules using a charged couple device (CCD). U.S. Pat. Nos. 5,466,348 and 6,203,981 disclose a method of increasing a ratio of signal to noise using a thin film transistor (TFT) with a circuit.

The use of the FET as a bio-sensor decreases costs and reduces the amount of time required to detect the bio-molecules, and the FET is easily used together with a process including an integrated circuit (IC)/MEMS.

FIG. 1A represents the prior art and schematically illustrates the structure of a conventional FET. Referring to the FIG. 1A, the FET includes a substrate 11 doped with an n-type or a p-type material, a source 12a and a drain 12b which are formed on both sides of the substrate 11 and doped to have the opposite polarity to the substrate 11, and a gate 13 on the substrate 11 that is in electrical communication with the source 12a and the drain 12b. Generally, the gate 13 includes an oxide layer 14, a poly silicon layer 15, and a gate electrode 16. Probe bio-molecules generally adhere to a surface 16a of the gate electrode 16, which face a reference electrode 17. The probe bio-molecule binds to a target bio-molecule through a hydrogen bond, or the like, and the bond is detected using an electrical method by the amount of electricity generated between the gate electrode 16 and the reference electrode 17.

FIG. 1B schematically illustrates a process of immobilizing probe bio-molecules 18 on a surface 16a of a gate electrode 16 of the FET illustrated in FIG. 1A and binding target bio-molecules with the probe bio-molecules 18. Referring to FIG. 1B, a current flowing through a channel varies according to the presence of the immobilized probe bio-molecules 18 on the surface of the gate electrode 16 and the presence of the bond between immobilized probe bio-molecules 18 and the target bio-molecules, and thus the target bio-molecules can be detected.

In general, more than two FETs are used to improve accuracy and sensitivity in a conventional method for detecting bio-molecules using the FET. Some of the FETs are used as reference FETs that do not react with the target bio-molecules and the others are used as sensing FETs that react with the target bio-molecules. The electric signal of the target bio-molecules can be obtained by subtracting the electric signals measured by the reference FETs from the electric signals measured in the sensing FETs on the assumption that noise signals are the same in the reference FETs and the sensing FETs.

For example, International Publication No. WO 03/062811 discloses a method of inferring a representative factor from comparing the data measured by two different sensors.

However, the assumption that noise signals are the same in the reference FETs and the sensing FETs is not reliable. In other words, although the FETs are manufactured by the same process to meet the same standard requirements, a wide range of variation occurs in the present FET manufacturing technology. Thus, the electric signals of the reference FET may be greater than that of the sensing FET.

SUMMARY OF THE INVENTION

The present invention provides a method of easily and accurately detecting the presence of bio-molecules and a concentration of the bio-molecules.

According to one aspect of the present invention, there is provided a method for detecting target bio-molecules using the same field effect transistor including: providing a first sample comprising a first target bio-molecule to a sensing surface of a field effect transistor and measuring a change in a first electric signal in the field effect transistor; providing a second sample to the sensing surface of the same field effect transistor and measuring a change in a second electric signal in the field effect transistor; and comparing the first electric signal with the second electric signal, wherein the field effect transistor includes: a substrate composed of a semiconductor material; a source region and a drain region which are formed to be separate on the substrate and doped to have the opposite polarity to the substrate; a channel region disposed between the source region and the drain region; an insulating layer which is disposed on the channel region and has the sensing surface composed of an electrically insulating material; and a reference electrode separated from and faces the insulating layer. The reference electrode is oppesdly disposed to the insulating layer.

In an embodiment of the present invention, the method may further include washing the sensing surface of the field effect transistor with a solution not containing bio-molecules before providing the second sample to the sensing surface of the field effect transistor.

The electric signal may include at least one of a drain current, a gate-source voltage, and a source-drain voltage.

The bio-molecule may be a nucleic acid or a protein.

The nucleic acid may be a polymerase chain reaction (PCR) product or a purified PCR product.

The first sample may include products resulting from a PCR amplification in the presence of a template and a primer, and the second sample may include the same PCR product as the first sample except without the template.

The ratio of the first electric signal and the second electric signal is calculated by comparing the first electric signal and the second electric signal.

The semiconductor material may be silicon and the electrically insulating material may be one of a silicon dioxide, a silicon nitride, a metal oxide such as for example, aluminum oxide, titanium dioxide, zirconia oxide, cerium oxide, or the like, or a combination comprising at least one of the foregoing electrically insulating materials.

In one embodiment, when the substrate is doped with an n-type material, the source region and the drain region is doped with a p-type material. In another embodiment, when the substrate is doped with a p-type material, the source region and the drain region is doped with an n-type material.

According to another aspect of the present invention, there is provided a method for detecting target bio-molecules using the same field effect transistor including: providing a plurality of samples, each having a known different bio-molecule concentration, between a sensing surface and a reference electrode of a field effect transistor and measuring electric signal changes in the field effect transistor; providing a sample having an unknown target bio-molecule concentration to the sensing surface of the field effect transistor and measuring an electric signal change in the field effect transistor; and comparing the electric signal change of the target bio-molecule with the electric signal changes of the plurality of samples. Based upon the electrical signal changes, the concentration of the target bio-molecule may be calculated or assumed. In the aforementioned method, the field effect transistor comprises: a substrate composed of a semiconductor material; a source region and a drain region which are formed to be separate on the substrate and doped to have the opposite polarity to the substrate; a channel region disposed between the source region and the drain region; an insulating layer which is disposed on the channel region and has a sensing surface; and a reference electrode disposed above and to be separate from the insulating layer. The reference electrode is opposedly disposed to the insulating layer.

In another embodiment of the present invention, the method may further include washing the sensing surface of the field effect transistor that acts as a gate with a solution not having bio-molecules between the procedures of providing samples to the sensing surface of the field effect transistor.

The electric signal may include at least one of a drain current, a gate-source voltage, and a source-drain voltage.

The bio-molecule may be a nucleic acid or a protein.

The nucleic acid may be a PCR product or a purified PCR product.

The semiconductor material may be silicon and the electrically insulating material may be one of a silicon dioxide, a silicon nitride, and a metal oxide.

In one embodiment, when the substrate is doped with an n-type material, the source region and the drain region is doped with a p-type material.

In another embodiment, when the substrate is doped with a p-type material, the source region and the drain region is doped with an n-type material.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art.

The presence of bio-molecules or a concentration of the bio-molecules can be detected using a field effect transistor without fixing bio-molecules.

Figure 1A:
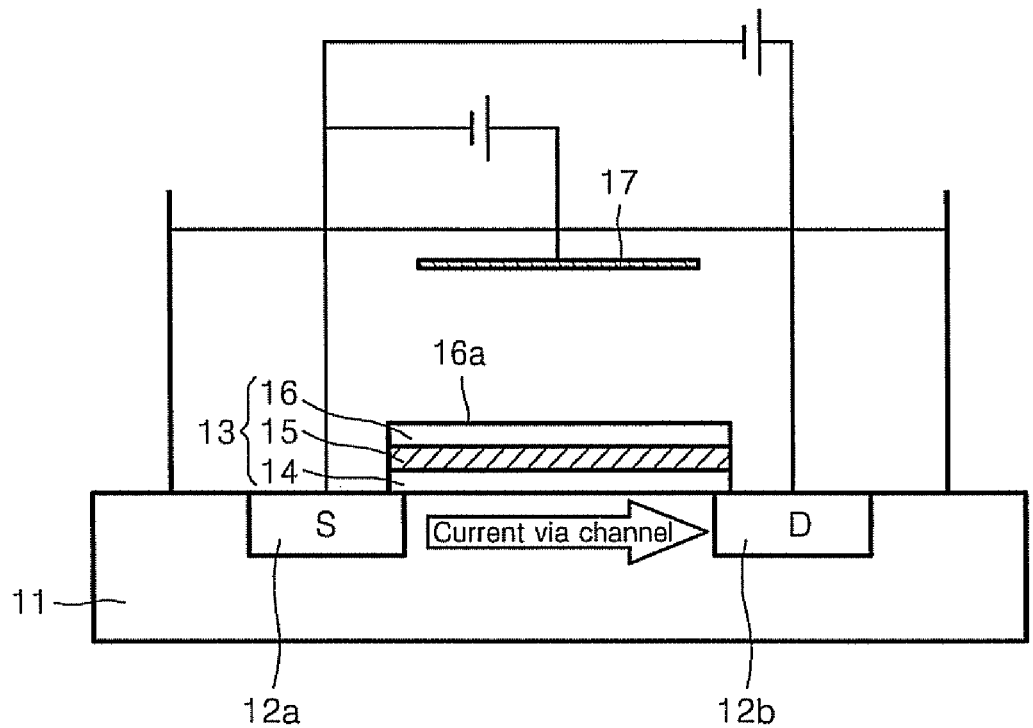
FIG. 1A represents prior art and schematically illustrates a structure of a conventional field effect transistor.
Figure 1B:
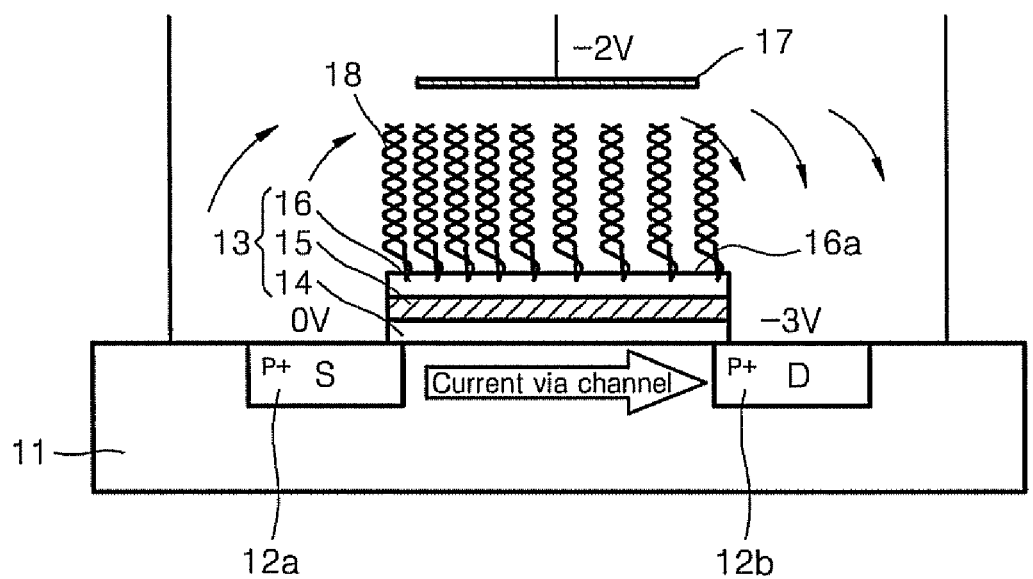
FIG. 1B represents the prior art and schematically illustrates a process of immobilizing probe bio-molecules on the surface of a gate electrode of the field effect transistor illustrated in FIG. 1A and binding target bio-molecules with the probe bio-molecules.
Figure 2:
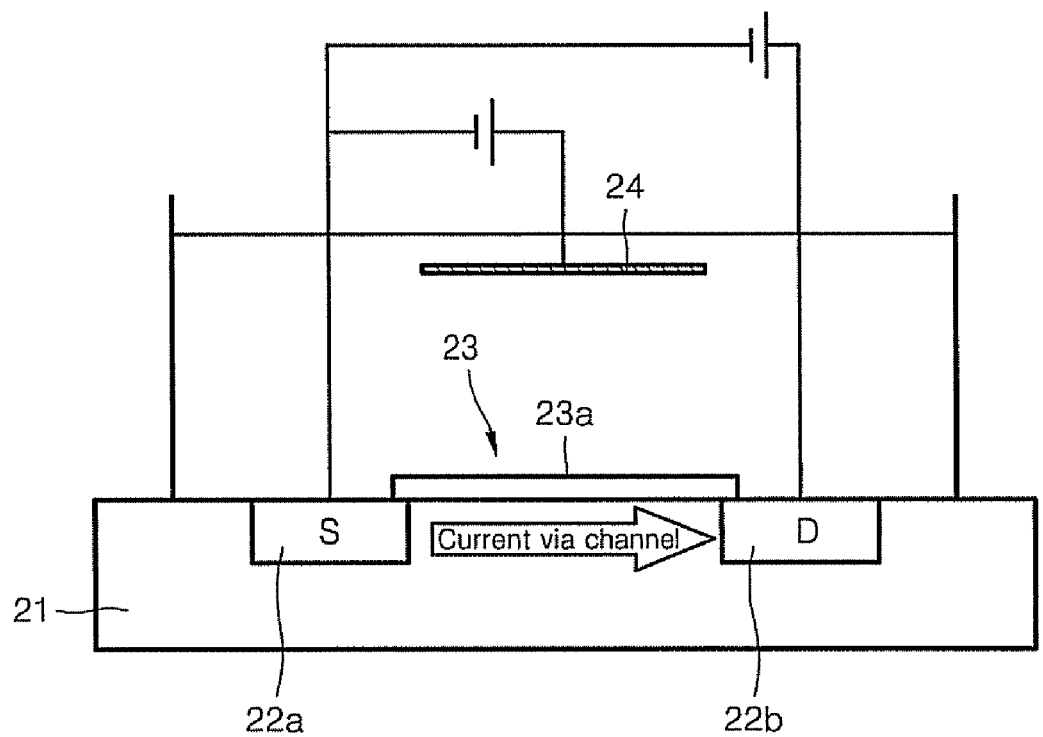
FIG. 2 schematically illustrates an exemplary embodiment of a structure of a field effect transistor used for detecting bio-molecules.

FIG. 2 schematically illustrates a structure of a field effect transistor used for a method of detecting bio-molecules.

Referring to FIG. 2, the field effect transistor used for the method of detecting bio-molecules includes: a substrate 21 composed of a semiconductor material; a source region 22a and a drain region 22b which are formed to be separate on the substrate 21 and doped to have the opposite polarity to the substrate 21; a channel region disposed between the source region 22a and the drain region 22b; an insulating layer 23 which is disposed on the channel region and has a sensing surface 23a; and a reference electrode 24 disposed above the insulating layer 23. The reference electrode 24 is opposedly disposed to the insulating layer 23 and is separated from it by a space as depicted in the FIG. 2.

The field effect transistor may be any field effect transistor that is commonly used in a conventional bio-sensor or in a complementary metal oxide semiconductor (CMOS) which can be a n-metal oxide semiconductor (n-MOS) or a p-metal oxide semiconductor (p-MOS). When the substrate 21 is doped with an n-type material, the source 22a and the drain 22b are doped with a p-type material. When the substrate 21 is doped with a p-type material, the source 22a and the drain 22b are doped with an n-type material.

In the field effect transistor, the source 22a may supply a carrier such as a free electron and/or a hole, while the drain 22b may be a region to which the carrier supplied by the source 22a reaches. The sensing surface 23a that acts as a gate may control the flow of the carrier between the source 22a and the drain 22b.

The semiconductor constituting the substrate 21 may comprise silicon, while the electrically insulating material constituting the insulating layer 23 may be any material on which bio-molecules are not fixed. In one embodiment, the electrically insulating material can be a metal oxide such as, for example, silicon dioxide, aluminum oxide, titanium dioxide, zirconia oxide or the like, or a combination comprising one of the foregoing metal oxides. In another embodiment, the insulating material can be silicon nitride. Alternatively, an additional layer composed of other material on which the bio-molecules are not fixed (e.g., do not bond or react) may further be formed on the insulating layer 23.

In one embodiment, the field effect transistor may be formed in the microchannel. Here, the substrate 21 may be included in the inner wall of the microchannel, and the gate electrode 24 may be disposed in the microchannel or on the inner wall of the microchannel.

According to an embodiment of the present invention, the presence of the target bio-molecule can be detected by comparing electric signals of samples using the same field effect transistor.

In the method, a first sample having a first target bio-molecule is brought into contact with or is brought into communication with the sensing surface of the field effect transistor and a first electric signal change of the field effect transistor is measured.

The bio-molecule may be a nucleic acid or a protein.

The "nucleic acid" is meant to comprehend various nucleic acids, nucleic acid analogues, and hybrids thereof. For example, the nucleic acid may be one of DNA, RNA, peptide nucleic acid (PNA), locked nucleic acid (LNA), and a hybrid thereof. The nucleic acid may also be an oligonucleotide or a polymerase chain reaction (PCR) product, and preferably a PCR product or a purified PCR product.

The protein may be one of an enzyme, a substrate, an antigen, an antibody, a ligand, an aptamer, a receptor, or a combination comprising one of the foregoing enzymes.

The electric signal may include at least one of a drain current, a gate-source voltage, and a source-drain voltage.

Next, the sensing surface and the reference electrode of the field effect transistor may be washed using a solution not containing any bio-molecules (e.g., a solution free of bio-molecules). The solution may be an electrolyte solution.

Following this, a second sample is disposed between the sensing surface and the reference electrode of the same field effect transistor, and a second electric signal change of the field effect transistor is measured.

The first sample may include products resulting from a PCR amplification in the presence of a template and a primer, and the second sample may include the same PCR product as the first sample except without the template. The second sample may also include PCR products having a different concentration from the first sample.

Then, the first electric signal is compared with the second electric signal. The signals can be compared in a various way according to types, characteristics, and concentration of the target bio-molecule. For example, the ratio of the first electric signal and the second electric signal is calculated using formula 1 below. Formula 1 compares the first electric signal with the second electric signal.

Compared signal=(the first electric signal)/(the second electric signal)   Formula 1

In another embodiment of the present invention, the concentration of the target bio-molecule can be detected by comparing the electric signals between samples using the same field effect transistor.

The field effect transistor may be used to detect the concentration of the target bio-molecule as described above.

In order to detect the concentration of the bio-molecule, a plurality of samples, each having a different bio-molecule concentration, are provided between an insulating layer and a reference electrode of a field effect transistor and electric signal changes of the field effect transistor are measured.

The bio-molecule may be a nucleic acid or a protein. The details are described above.

The electric signal may include at least one of a drain current, a gate-source voltage, and a source-drain voltage.

Then, a sample having an unknown target bio-molecule concentration is brought into contact with the sensing surface of the same field effect transistor and electric signal changes of the field effect transistor are measured.

The gate electrode of the field effect transistor can be optionally washed by providing a solution free of bio-molecules to the gate electrode between the procedures of providing the samples.

Then, the electric signal changes of the target bio-molecule are compared with the electric signal changes of the plurality of samples, and the concentration of the target bio-molecule is calculated.

The method of detecting the bio-molecules according to an embodiment of the present invention can be used to detect PCR products. PCR would occur if there are target bio-molecules in the sample, but PCR would not occur if there are no target bio-molecules in the sample. The presence of target bio-molecules and the concentration of the bio-molecules in the sample can be detected by detecting PCR product using the method.

In a conventional process using a conventional field effect transistor, the possibility of an error in detecting bio-molecules was high since the sensitivity and efficiency are different among the field effect transistors. However, the method of detecting bio-molecules can overcome the problems that are produced in a conventional field effect transistor. That is, the bio-molecules can accurately and easily be detected using the method of detecting bio-molecules according to an embodiment of the present invention. In addition, since the bio-molecules are not bonded or attached to the field effect transistor, the field effect transistor can be easily manufactured. Difficulties in the manufacturing of the field effect transistors (brought about by the bonding of the molecules to the surface of the field effect transistors) are therefore minimized.

Hereinafter, the present invention will be described more specifically with reference to the following Examples. The following Examples are for illustrative purposes and are not intended to limit the scope of the present invention.

EXAMPLE 1

Preparation of a Field Effect Transistor Based Bio-Sensor

A field effect transistor device was prepared using a XC10-1.0 um CMOS process and equipment of X-FAB Semiconductor Foundries (Germany). A silicon oxide insulating layer 23 was formed on a channel between a source and a drain. The insulating layer 23 having a sensing surface 23a was formed by patterning the silicon oxide, and a reference electrode 24 disposed above and to be separate from the sensing surface 23a was formed to prepare a field effect transistor as illustrated in FIG. 2.

Then, the surface of the field effect transistor including the exposed sensing surface 23a and the reference electrode 24 was carefully washed with pure acetone and deionized water and dried. A wet station that is used in a semiconductor manufacturing process was used in washing the substrate. Then, the substrate was dried using a spin dry method.

EXAMPLE 2

Detection of PCR Products Using Field Effect Transistor Based Bio-Sensor

This example was conducted to determine whether a 4×12 field effect transistor based bio-sensor array manufactured in Example 1 could detect a PCR product.

For this, PCR products, a washing buffer, and a negative control (NTC) were alternatively brought into contact with the field effect transistor based bio-sensor.

Figure 3:
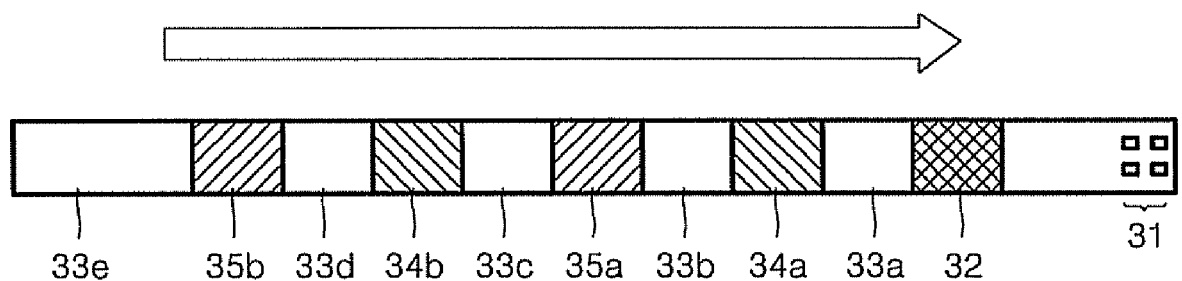
FIG. 3 schematically illustrates an exemplary embodiment of a procedure of alternatively providing PCR products, a washing buffer, and a negative control (NTC) to a sensing surface of the field effect transistor.

FIG. 3 schematically illustrates a procedure of alternatively providing PCR products and a washing buffer, and a NTC between the sensing surface and the reference electrode of the field effect transistor of an embodiment of the present invention. Referring to FIG. 3, a calibrant solution 32, a washing solution 33a, a PCR product 34a, a washing solution 33b, an NTC 35a, a washing buffer 33c, a PCR product 34b, a washing solution 33d, an NTC 35b, and a washing buffer 33e are brought into contact with at least one field effect transistor based bio-sensor 31.

0.1 mM NaOAc was used as the calibrant solution in the Examples.

The calibrant solution is used to identically set the conditions of the field effect transistors.

0.01 mM phosphate buffer (pH 6.04) was used as the washing solution in Examples.

*Staphylococcus aureus* as a template was amplified through a PCR amplification to obtain the PCR product used in Examples. The base sequence of the forward primer was 5'-(TAG CAT ATC AGA AGG CAC ACC C)-3', and the base sequence of the reverse primer was 5'-(ATC CAC TCA AGA GAG ACA ACA TT)-3'. The amplified PCR product had a size of 240 bp, the pH of the phosphate buffer including the PCR product was 6.47, and the concentration of the PCR product was 5 ng/µl (nanograms per microliter).

In addition, the NTC solution was used to remove the template in the PCR and inhibit producing the PCR product, and thus to identify an inhibition of a material other than the PCR product. The PCRs are performed in the same manner as in Example 1, except that the template was not added. The concentration of the PCR product was unknown since PCR amplifications did not occur after the PCR. This experiment is intended for a case that PCR has not performed since the target DNA was not included in the sample.

PCR products, a washing buffer, and a negative control (NTC) were alternatively provided between the sensing surface and the reference electrode of the field effect transistor according to the procedure illustrated in FIG. 3. Averages and standard deviations of the current changes of the PCR product and current changes of the NTC obtained from 48 same field effect transistor based bio-sensors were calculated using Formula 2. The results are shown in Table 1

Compared current=(current change of PCR product)/
(current change of NTC)   Formula 2

It was measured whether the pH difference between the solution including PCR products and the washing solution influenced the current changes. The pH difference between the PCR product and the washing solution was 0.43, and thus the current change due to the pH difference can be ignored.

As shown in Table 1, the PCR product and the NTC were effectively detected according to the method and the results are significant since the standard deviation is low.

COMPARATIVE EXAMPLE 1

Detection of PCR Products Using Field Effect Transistor Based Bio-Sensor

The experiments were performed in the same manner as in Example 1. Averages and standard deviations of the current changes of the PCR product and current changes of the NTC obtained from any two of 48 same field effect transistor based bio-sensors were calculated using Formula 2. The results are shown in Table 1 below.

As shown in Table 1, the PCR product and the NTC were not significantly detected according to the method since the standard deviation is too high.

TABLE 1

|  | Average | Standard deviation |
|---|---|---|
| Example 2 | 4.28 | 1.78 |
| Comparative Example 1 | 4.94 | 4.03 |

EXAMPLE 3

Detection of Concentration of PCR Products Using Field Effect Transistor Based Bio-Sensor It was determined whether a field effect transistor based bio-sensor manufactured in Example 1 could detect the concentration of a PCR product.

For this, a plurality of PCR products, each having a different concentration, and a washing buffer were alternatively provided to the field effect transistor based bio-sensor.

Figure 4A:
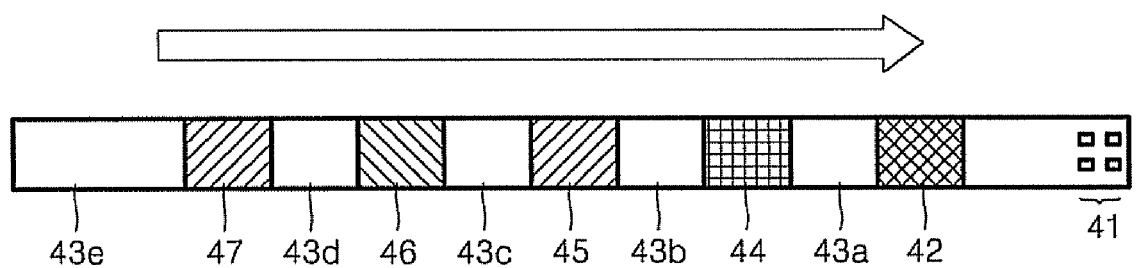
FIG. 4A schematically illustrates an exemplary embodiment of a procedure of alternatively providing a plurality of PCR products, each having a different concentration, and a washing buffer to a sensing surface of the field effect transistor.

FIG. 4A schematically illustrates a procedure of alternatively providing a plurality of PCR products, each having a different concentration and a washing buffer to the sensing surface of the field effect transistor of an embodiment of the present invention. Referring to FIG. 4A, 10 ng/µl of a PCR product 42, a washing solution 43a, 5 ng/µl of a PCR product 44, a washing solution 43b, 1 ng/µl of a PCR product 45, a washing solution 43c, 0.5 ng/µl of a PCR product 46, a washing solution 43d, 0.25 ng/µl of a PCR product 47, and a washing solution 43e were provided to at least one field effect transistor based bio-sensor 41.

The washing solution and the PCR products are the same as those used in Example 1.

Figure 4B:
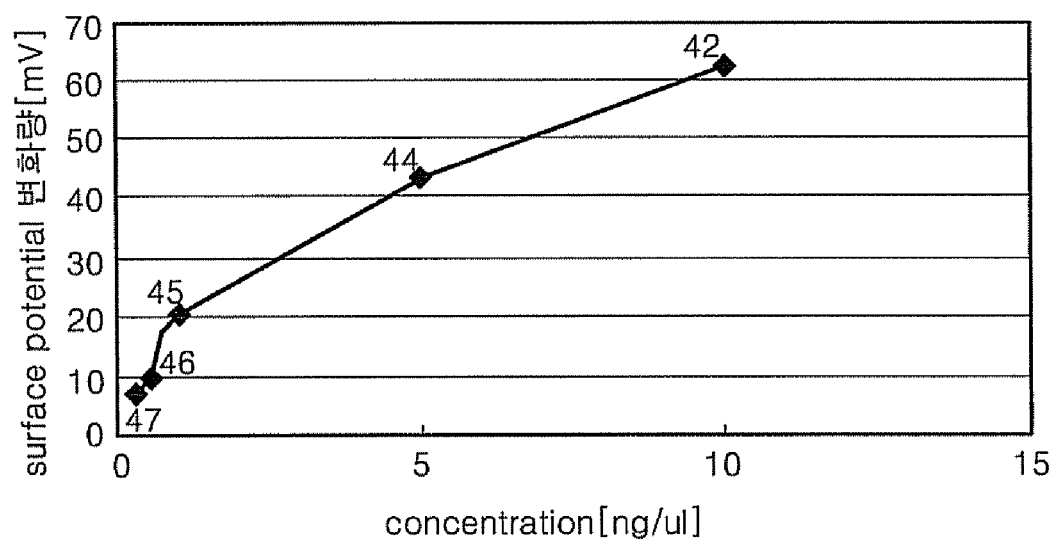
FIG. 4B is a graph illustrating a voltage change when the PCR products having different concentrations and a washing buffer are alternatively provided to a sensing surface of the field effect transistor as shown in FIG. 4A.

FIG. 4B is a graph illustrating a voltage change when a plurality of PCR products, each having a different concentration and a washing buffer are alternatively provided to the sensing surface of the field effect transistor in the procedure as shown in FIG. 4A.

Referring to FIG. 4B, the concentration of the PCR products is relative to the surface current changes. Accordingly, a PCR product having an unknown concentration is provided to the same field effect transistor to obtain a surface current change. Then, the surface current change is compared with the values in FIG. 4B to obtain the concentration of the PCR product.

The present method reduces the number of errors that occur when conventional field effect transistors are used because the sensitivity and efficiency are different among the conventional field effect transistors. In other words, bio-molecules can accurately and easily be detected using the method of detecting bio-molecules according to the present invention. In addition, since the bio-molecules are not bonded onto the field effect transistor, the field effect transistor can be simply manufactured and the difference of characteristics between the field effect transistors that is caused by additional process can be reduced.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of detecting target bio-molecules using the same field effect transistor, the method comprising:
    contacting a first sample having known target bio-molecules with a sensing surface of a field effect transistor;
    measuring a first electric signal of the field effect transistor;
    contacting a second sample with the sensing surface of the same field effect transistor;
    measuring a second electric signal of the field effect transistor; and
    comparing the first electric signal with the second electric signal,
    wherein bio-molecules are not fixed on the sensing surface and wherein the field effect transistor comprises: a substrate composed of a semiconductor material; a source region and a drain region which are formed to be separate on the substrate and doped to have a polarity opposite to a polarity of the substrate; a channel region disposed between the source region and the drain region; an insulating layer which is disposed on the channel region and has the sensing surface; and a reference electrode oppositely disposed to the sensing surface; wherein the reference electrode is separated from the insulating layer, and wherein the comparing of the first electric signal with the second electric signal comprises calculating a compared signal according to Formula (I) below Compared signal=(the first electric signal)/(the second electric signal).

2. The method of claim 1, further comprising washing the sensing surface of the field effect transistor with a solution free of bio-molecules before contacting the second sample with the sensing surface of the field effect transistor.

3. The method of claim 1, wherein the first electric signal and the second electric signal comprise at least one selected from the group consisting of a drain current, a gate-source voltage, and a source-drain voltage.

4. The method of claim 1, wherein the each of the known target bio-molecules is a nucleic acid or a protein.

5. The method of claim 4, wherein the nucleic acid is a polymerase chain reaction (PCR) product or a purified PCR product.

6. The method of claim 1, wherein the first sample comprises products resulting from a PCR amplification in the presence of a template and a primer, and the second sample comprises the same PCR product as the first sample except that the first sample is without the template.

7. The method of claim 1, wherein the semiconductor material is silicon and the electrically insulating material is a metal oxide.

8. The method of claim 7, wherein the metal oxide is silicon oxide, titanium oxide, zirconia oxide, aluminum oxide, cerium oxide, or a combination comprising at least one of the foregoing metal oxides.

9. The method of claim 1, wherein the insulating layer is composed of silicon nitride.

* * * * *